(12) United States Patent
Shapiro

(10) Patent No.: US 10,426,333 B2
(45) Date of Patent: Oct. 1, 2019

(54) DIRECTIONAL ILLUSIONS BASED ON MOTION PIXELS AND USES THEREOF

(71) Applicant: Arthur Shapiro, Rockville, MD (US)

(72) Inventor: Arthur Shapiro, Rockville, MD (US)

(73) Assignee: AMERICAN UNIVERSITY, Washington, DC (US)

( * ) Notice: Subject to any disclaimer, the term of this patent is extended or adjusted under 35 U.S.C. 154(b) by 0 days.

(21) Appl. No.: 14/873,973

(22) Filed: Oct. 2, 2015

(65) Prior Publication Data

US 2016/0095513 A1    Apr. 7, 2016

Related U.S. Application Data

(63) Continuation-in-part of application No. 13/775,875, filed on Feb. 25, 2013, now abandoned.

(60) Provisional application No. 61/602,137, filed on Feb. 23, 2012.

(51) Int. Cl.
*A61B 3/032* (2006.01)
*A61B 3/024* (2006.01)
*A61B 3/113* (2006.01)
*A61B 3/02* (2006.01)
*G02F 1/01* (2006.01)

(52) U.S. Cl.
CPC ............ *A61B 3/032* (2013.01); *G02F 1/0123* (2013.01)

(58) Field of Classification Search
CPC ... A61B 3/1015; A61B 3/1225; A61B 3/1208; A61B 3/032; A61B 3/024; A61B 3/103; A61B 1/05; A61B 1/00183; A61B 5/16; A61B 3/113; G02F 1/0123

USPC .............. 351/205, 211, 221, 222, 223, 246; 600/173, 558

See application file for complete search history.

(56) References Cited

U.S. PATENT DOCUMENTS

| | | | | |
|---|---|---|---|---|
| 5,920,374 A | * | 7/1999 | Vaphiades | A61B 3/028 348/E13.037 |
| 2003/0081176 A1 | * | 5/2003 | Stewart | A61B 3/024 351/223 |
| 2008/0024725 A1 | | 1/2008 | Todd | |
| 2011/0242486 A1 | * | 10/2011 | Ebisawa | G06F 3/013 351/206 |

OTHER PUBLICATIONS

Shapiro et al "Visual illusions based on single<field contrast asynchronies"; Journal of Vision (2005) 5, p. 764-782.*

* cited by examiner

*Primary Examiner* — Jie Lei
(74) *Attorney, Agent, or Firm* — Thompson Hine LLP

(57) ABSTRACT

The present invention relates to a means for creating a visual illusion of directional movement based on stationary motion elements referred to as "motion pixels." In various embodiments, methods for using the directional illusion are provided, such as 1) the measurement and/or assessment of visual performance in active and virtual reality environments, 2) the measurement and/or assessment of acuity, in conjunction with eye trackers so as to measure visual performance in nonverbal or potentially malingering observers, 3) the enhancement of advertising and marketing by drawing attention to a desired symbol, and 4) the enhancement of images so as to produce the appearance of motion in otherwise stationary images.

8 Claims, 3 Drawing Sheets

Subelement
1 2 3

Subelement
1 2 3 4 5

Pixel subelements
1 2 3
4 5 6
7 8 9

DIRECTIONAL ILLUSIONS BASED ON MOTION PIXELS AND USES THEREOF

This application is a Continuation-in-part of co-pending U.S. patent application Ser. No. 13/775,875, filed Feb. 25, 2013, which claims priority to U.S. Patent Application Ser. No. 61/602,137 filed Feb. 23, 2012, each of which is expressly incorporated by reference herein in its entirety.

The present invention relates to means for creating a visual illusion of movement. In one embodiment, the invention provides methods for using a directional illusion for the measurement and/or assessment of visual performance and/or acuity. In another embodiment, the invention further provides an apparatus or arrangement for evaluating visual performance in various settings. In other embodiments, the directional illusion has other applications, such as enhancing advertising and marketing by drawing attention to a desired symbol; enhancing images, such as personal digital photos; and video games.

BACKGROUND OF THE INVENTION

A visual illusion (also called an optical illusion) is characterized by visually perceived images that differ from objective reality. The information gathered by the eye is processed in the brain to give a perception that does not tally with a physical measurement of the stimulus source. There are three main types: literal optical illusions that create images that are different from the objects that make them; physiological optical illusions that are the effects on the eyes and brain of excessive stimulation of a specific type (brightness, color, size, position, tilt, movement); and cognitive optical illusions, the result of unconscious inferences.

Motion perception is responsible for a number of sensory illusions. Film animation is based on the illusion that the brain perceives a series of slightly varied images produced in rapid succession as a moving picture. Likewise, when we are moving, as we would be while riding in a vehicle, stable surrounding objects may appear to move. We may also perceive a large object, like an airplane, to move more slowly than smaller objects, like a car, although the larger object is actually moving faster. The Phi phenomenon is yet another example of how the brain perceives motion, which is most often created by blinking lights in close succession. The perception of motion can also be created by what has been termed "reversed phi," in which two lights of opposite contrast polarity are alternated to create the appearance of motion in the direction opposite to that predicted by Phi. Others have used phi and reverse phi to create the appearance of continual motion (i.e., illusory motion perpetually moves in one direction) by juxtaposing two images and slightly offset negatives (referred to as four-stroke motion) or by inserting a gray frame between two slightly offset lights (referred to as two-stroke motion). In addition, non-continual motion can be created by modulating the luminance of thin lines at edges surrounding objects: if a gray rectangle is bordered on the left by a thin white line and on the right by a thin black line, then modulating the luminance of a field surrounding the rectangle will make the rectangle appear to shift back and forth; i.e., when the surrounding field is bright, the rectangle appears to shift to the right, and when the surrounding field is dark, the rectangle appears to shift to the left. The motion arises even though the rectangle and the edges are physically stationary.

Here we present two types of visual displays that lead to the perception of perpetual motion but do not create changes in physical space—that is, continual motion from physically stationary objects. In other words, the displays combine the perceptual motion found in reverse phi phenomena with the thin edges found in edge motion conditions. The key insight into these conditions is that motion signals can be created by modulating the luminance of thin edges in relation to the phase of luminance modulation of fields that surround the edge. When viewing displays that combine opposite direction motion signals, the visual system will group the display into the perception of a moving object. A motion signal is created by changing the modulation at the edge of the field.

Traditional vision acuity tests have used static optotypes as displays of printed or projected characters, objects, or shapes. Numerous patterns, configurations, and methods for static optotypes have been proposed for testing acuity based upon the ability of a subject to distinguish these various shapes, sizes, contrasts, and colors in tests such as Snellen charts, tumbling "E" arrays (static images of the letter "E" where the static image is also rotated 90 degrees, 180 degrees, and 270 degrees for discernment), Landolt "C" charts, and so on. Certain prior art vision testing patterns use periodic images, such as disks, rectangles, diamonds, etc.; others are quasi-periodic, such as tri-bar, and small checkerboard designs.

While the Landolt "C" chart is the clinical standard for acuity, the familiar Snellen eye testing chart as developed in 1862 using large, black, serifed letters on a white background is the test frequently used for determining visual acuity. The concept of these charts to verify acuity is based upon the patient seeing patterns such as letters or printed images on those charts. Snellen's standard is that a person should be able to see and identify a 3.5 inch letter at a 20 foot distance (that ratio being consistent regardless of its use in the "English" or Metric system). A disadvantage of the Snellen-type images is that even defocused letters can still be partially recognized by their blur patterns. Much time is thus wasted as the patient, whose eyes are being tested, attempts to guess the letter. The design of the Snellen chart is further complicated by each letter having a different degree of recognizability and by the tendency of the patient to strain to perceive coherency when trying to identify the letters.

Thus, most visual testing systems are intended for optometry offices where there are precise optical devices that can be used to measure visual function with conscious articulate observers. However, it is often important to give quick assessment of visual function in active environments, such as for sports activities, military training or in conditions of high attention load, or for observers who are unable to respond in conventional ways (e.g. infants, non-communicative severely disabled patients or patients suffering from head trauma or other forms of dementia, or observers who are intentionally trying to deceive the tester (malingerers), or sometimes there may be the desire to test observer acuity covertly or without observers being aware that they are undergoing an examination.

The visual displays presented here have three features that make them useful for optical testing in situations other than in the standard optometry setting with conscious articulate observers: 1. The illusory motion depends upon the appearance of edges that change their luminance levels over time (i.e. they change from light to dark and back to light). For observers with normal visual acuity, the edges can produce the appearance of motion even when the edges are remarkably thin. Observers with normal visual acuity can see motion when the edges are as thin as 0.1 min of visual angle, but the poorer an observers visual acuity the thicker edges need to be in order to see the illusory motion. As a general rule, if observers can discern the edges, then they will be able to see motion. Hence, the appearance of motion can be taken as a measure of an observer's ability to see detail. 2. The perpetual motion created by the illusion drives eye movements in the direction of the motion even though all objects in the display are physically stationary. Observers' eye movements therefore give an indication of whether or not the observers are able to discern the edges. 3. The illusions (and eye-tracking) can be displayed on any monitor system and in conjunction with other images. The illusions (and eye-tracking) can therefore be displayed on phones, computer monitors, virtual reality headsets, etc., to test visual function.

These three features of the visual displays presented here allow visual function to be assessed in a wide variety of conditions where assessment is desired, but verbal (or gestural) response is impossible or misleading. This may occur, for instance, with elderly, dementia, or infant populations, or conditions with high attentional load (pilots or sports), or conditions in which a verbal response may be deceptive (for instance, people trying to be excused from military service by claiming poor eye sight). Our new eye-tracking test eliminates issues from non-verbal, non-gestural, and deceptive observers, as eye movements in the direction of the illusory motion will occur naturally and involuntarily when the movement is seen.

SUMMARY OF THE INVENTION

In one aspect of the invention, a visual directional illusion is provided, in which a stationary displayed object appears to move. The observer's perception of movement of objects on a screen is created by means of changes in temporal luminescence, contrast, width, and temporal phase at the edges of the displayed object and/or the surrounding field.

In another aspect of the invention motion can be reduced to individual elements that create motion at a local portion of the display device. Even though the elements are stationary, by placing many elements on the screen, an observer with good visual acuity will see the appearance of a shape moving in a predetermined direction.

In another aspect of the invention, a dynamic visual acuity assessment method is provided, where various parameters of the directional illusion are varied, and an observer responds to these changed parameters. This aspect of the invention can be carried on any display monitor, including virtual reality headsets and phones.

In another aspect of the invention, a method for enhancing a displayed image is provided, where the image exhibits the directional illusion.

In another aspect of the invention, observers view the motion illusions in the presence of an eye tracker. Since eyes automatically follow the illusory motion, the technique can be used to test visual function without verbal response.

DETAILED DESCRIPTION

In real motion, a light or an object physically moves from one place to another. In some motion illusions, motion is driven by the appearance of one light and the disappearance of another. In some forms of reverse phi motion, light is generated at an edge, but the contrast of the whole image is changed from positive to negative.

The illusions shown here are created by reducing the motion to its elemental form (i.e., a change in contrast at an edge or even between two pixels) and then used in combination with stationary objects or by arranging the elements to create a global percept.

Figure 1:
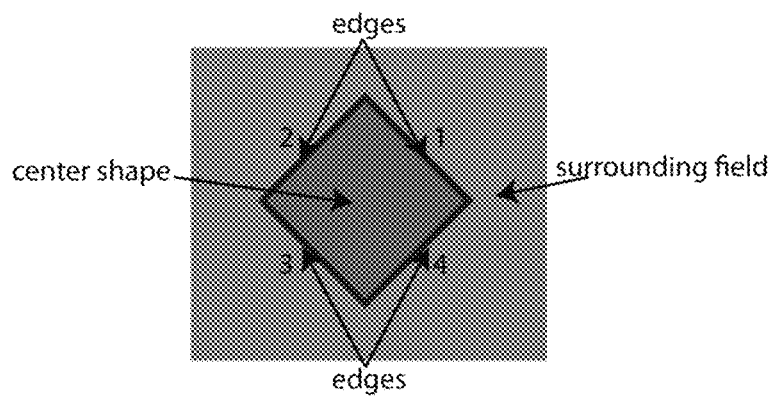
FIG. 1 shows a schematic of one embodiment of the invention.
Figure 4A:
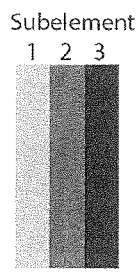
FIG. 4A shows a configuration where subelement 2 remains steady whereas subelements 1 and 3 are in quadrature phase.
Figure 4B:
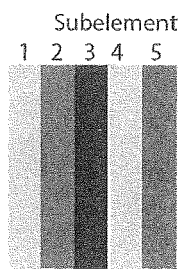
FIG. 4B shows a configuration where subelement 3 remains steady whereas each of subelements 1, 2, 4, and 5 are in quadrature phase.
Figure 4C:
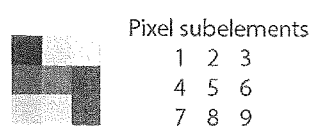
FIG. 4C shows an element composed of a grid of nine sub-elements, wherein center pixel subelement 5 remains steady.

The elemental components that create local motion are referred to as "motion pixels." That is, motion pixels are the elements, such as those shown in FIG. 4, or the combination of features, such as the edges of the diamond in FIG. 1. Each motion pixel is stationary but creates in the brain's visual system a motion signal at a particular location. By altering the modulation phase of the sub-elements, motion pixels can specify motion in the same way that a pixel of typical display takes on a particular color (i.e., Red, Green, or Blue). By combining the motion pixels we can create moving global shapes or surrounding shapes.

The use of the described motion pixels differs significantly with previous methods for creating the perception of motion. For example, the use of three or more elements, such as three or more sub-element motion pixels, are not found in the research literature, which customarily only have two elements. Also, motion pixels reduce continuous motion to elemental form and are therefore fundamentally separate from the objects or images used in standard reverse phi demonstrations. Further, motion pixels allow construction of global objects of a wide variety of shapes and forms, or can be added to other objects in an image. Thus, the use of motion pixels allow the construction of forms that can be used in tests that are experimentally sound: that is, rather than asking observers "do you see the elements?", the forms can be generated to allows questions for which there are correct answers, such as "is the motion moving up down left or right?". This also has the benefit of removing observer judgment bias since it is not asking the observer to give an evaluation of their percept, per se, but rather about an aspect of the stimulus that can corresponds to a physical aspect of the stimulus (in this case the temporal phase relationships of the sub-elements of the motion pixel).

Because observers with normal acuity can perceive motion when the motion pixels are fine (0.1 min of visual angle), we can use the motion pixels to assess acuity in novel conditions. Indeed, 0.1 min of visual angle is referred to as hyperacuity in humans (hyperacuity refers to "a sensory capability that transcends sampling limits set by discrete receiving elements"). Observers with no need for optical correction can discern the direction of motion for edges whose image on the back of the eye subtends an angle that is much narrower than the width of a single cone photoreceptor.

In one aspect of the invention, an optical or visual illusion is provided, which gives the impression of movement to an observer. In one embodiment, the illusion comprises a center shape having edges that border the center shape, and a surrounding field, as shown in FIG. 1. In one embodiment, an illusion of movement is created by small, e.g., 10 degrees at 3 Hz modulation, temporal phase and/or contrast changes in thin edges (e.g., <1 minute of visual angle) surrounding the center shape, which creates an observer's perception of directional movement of the center shape.

In FIG. 1, the directional illusion where the center shape is a diamond, which is convenient because it has four sides and is oriented obliquely, but other shapes can also be used: for instance, an arc-shape can be used to create the appearance of clockwise and counter-clockwise motion. The center shape can be any hue, but the luminance should be between the maximum and minimum luminance of the edges and the surrounding field. Unlike the edges and the surrounding field, the luminance of the center shape does not change over time. The objects of the illusion, i.e., center shape, edges, and surrounding field, can be presented or depicted in any suitable format, such as being displayed on a CRT or LCD monitor.

Figure 2:
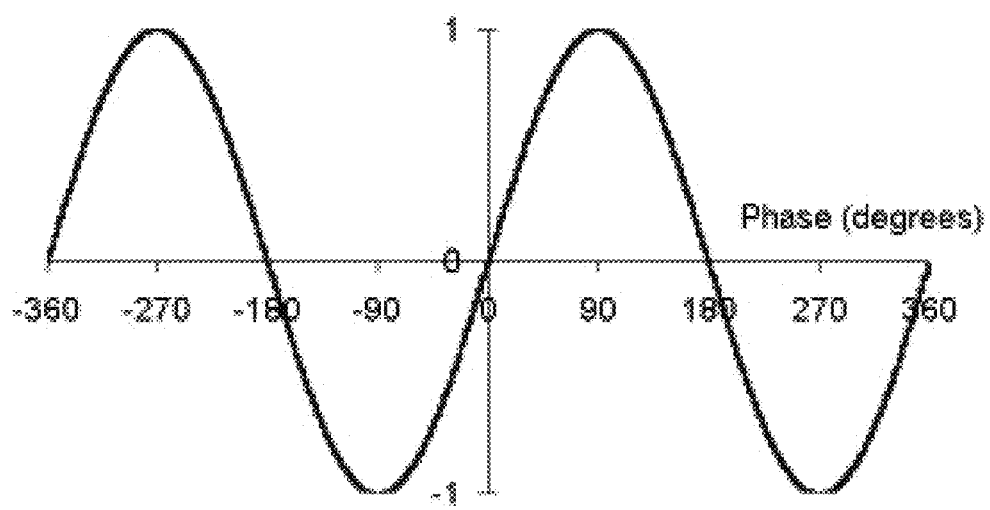
FIG. 2 shows a sine wave representing changes in a characteristic of at least one of the edges, in one embodiment of the invention.

In this instance the motion pixels occur at the edges of the diamond in conjunction with the surrounding field. There are two aspects of the edges that may be changed over time: a) luminance and b) the width of the edges. In one embodiment, the luminance of the edges changes over time such that the edges become light and dark and then repeat. The profile of the luminance change can be described as a sine wave with the luminance on the y-axis and time on the x-axis, as shown schematically in FIG. 2. There are four parameters of the sine wave that can be used to control the light to dark pattern: mean, amplitude, frequency and phase. In one embodiment, the mean luminance level of the edge is substantially similar to the luminance level of the center shape. The amplitude of the sine wave describing the temporal changes in luminance of the edges may be variable. The illusory motion gets stronger as the amplitude gets larger; however, this effect co-varies with the amplitude of the surrounding field, as described below. In various embodiments, the illusion occurs when the frequency of the modulation of the edges is between about 1 Hz and about 8 Hz. Faster rates, e.g., higher frequencies, may also be employed, but in some cases, the frequency is limited by the capabilities of CRT and LCD monitors. Lastly, the phase, which represents the edge changes relative to changes in the surrounding field, may also be manipulated for creating the illusion of directional motion.

As described above, the width of the edges also play a role in the creation of the illusion. The illusion of motion can be perceived when the edges are thin, i.e., approximately 0.1 min of visual angle in normal observers. The ability to see the motion when the edges are thin depends upon the observer's visual acuity.

Figure 3:
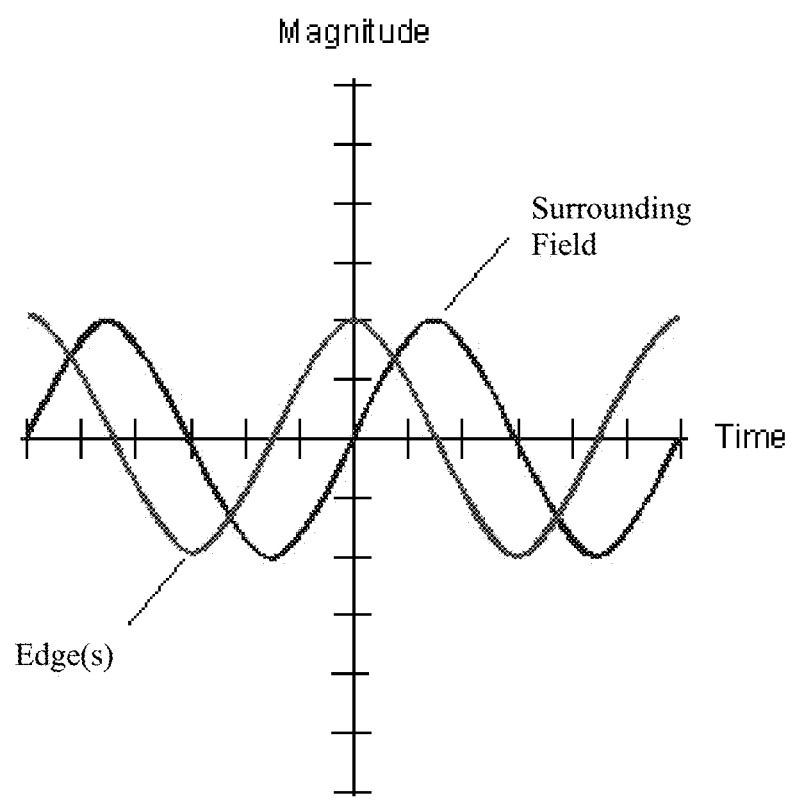
FIG. 3 shows a phase shift between the changes in at least one of the edges and the changes in the surrounding field, in one embodiment of the invention.

As with the edges, the luminance of the surrounding field changes over time in a sinusoidal fashion, for example, as shown in FIG. 3. There are four parameters for the sine wave that control the light to dark pattern: mean, amplitude, frequency and phase. In one embodiment, as with the edges, the mean luminance level of the surrounding field is substantially similar to the luminance level of the center shape.

The amplitude of the sine wave describing the temporal changes in luminance of the surrounding field may be variable. The illusory motion gets stronger as the amplitude gets larger; however, this effect co-varies with the amplitude of the edges. In one embodiment, the frequency of modulation matches the frequency of the edge modulation. Lastly, as described in detail below, the phase, which represents the edge changes relative to changes in the surrounding field, is manipulated to create the illusion of directional motion. In one embodiment, the temporal phase of the surround is defined as 0 degrees, and the bottom edges modulate at −90 degrees while the top edges modulate at +90 degrees. In this case, the apparent motion inside the center object is upward. If the temporal phase of the surround is shifted to 180 degrees, the motion will be downward. The size of the surrounding field does not matter, as long as its spatial extent is larger than the center field and the edges.

The center object, which will be perceived as moving by the described changes in edge and surrounding field, can be any shape, such as geometric figures or real-world objects, such as a picture of a baseball or a football.

The perception of directional motion can be manipulated by varying the parameters described above, for example, by varying the phase and/or contrast between the edges and the surrounding fields. For example, by changing the temporal phase relationship between the edges and the surrounding field, the center shape will appear to be moving up, down, left, right, inward or outward. In the case of the diamond shown in FIG. 1, if the phase of the luminance changes of the edges are varied relative to the changes in the surrounding field, a directional illusion is created in one of six directions, as shown in the table below.

| Perceived direction | Phase of edge modulation relative to the surrounding field modulation | | | |
| --- | --- | --- | --- | --- |
| of the diamond | Edge 1 | Edge 2 | Edge 3 | Edge 4 |
| Upward | Lead 90° | Lead 90° | Trail 90° | Trail 90° |
| Downward | Trail 90° | Trail 90° | Lead 90° | Lead 90° |
| Left | Trail 90° | Lead 90° | Trail 90° | Lead 90° |
| Right | Lead 90° | Trail 90° | Lead 90° | Trail 90° |
| Inward | Trail 90° | Trail 90° | Trail 90° | Trail 90° |
| Outward | Lead 90° | Lead 90° | Lead 90° | Lead 90° |

In the above table, a complete cycle of the sine wave represents 360 degrees. Thus, a variance in the phase between the edge and surrounding field of 90 degrees represents a quarter of a cycle. In other words, the cyclic variation of the luminance of the edge is shifted either to the left, and occurs earlier in time, or is shifted to the right, and occurs later in time, in relation to the modulation of the surrounding field.

In one embodiment, multiple center shapes, each with edges, can be placed in the surrounding field. For example, the center shapes may be arranged in a circular pattern, such that creating the illusion of movement of the center shapes creates the illusion that the circular pattern is itself rotating, where the rotation can be created to be either clockwise, counterclockwise, or alternating between the two directions.

In another embodiment, motion is created by combining discrete local motion elements—that is, for example, using samples from the edges in the diamond described above, and making these samples small, and then spreading the samples over distances to form a shape.

The local samples do not have to follow the exact pattern of the diamond's edges but can be elements composed of a number of sub-elements that modulate in time (e.g., pixels or lines). One crucial feature is that one sub-element modulates in time approximately 90 degrees ahead of or behind another sub-element. The 90-degree temporal relationship is referred to as having the elements that modulate in quadrature phase with each other.

FIGS. 4 A, B, and C shows three ways of constructing motion elements that are slightly different from the motion edges shown in the diamond example above but nonetheless still create the appearance of continual motion. These motion elements work because the modulation of the contrast between the sub-elements (in quadrature phase) creates local motion energy that moves perpetually in a particular direction. In panel A, the sub-elements (1 and 3) are two lines (or pixels) surrounding a center mid-luminance line or pixel (sub-element 2). When the luminance of sub-element 3 modulates 90 degrees ahead of the luminance of sub-element 1, the motion will move towards element 3, and vice versa. Panel B shows an element created by the comparison of two motion signals. Two sub-elements (1 and 2) and (4 and 5) sit on either side of a mid-luminance line or pixel (sub-element 3). This element is useful because local change of contrast can quickly change the perceived direction of the local motion. Panel C shows an element composed of a grid of nine sub-elements. By modulating the luminance of the sub-elements on either side of the center pixel, the local motion can be made to change in any direction.

Figure 5:
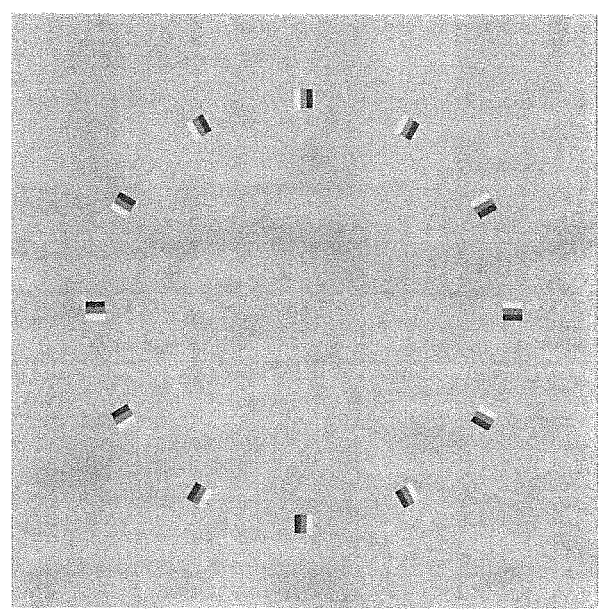
FIG. 5 shows motion elements configured into an example of a global shape using local motion elements arranged in a circle, which can give said circle the appearance of rotating, even though the subelements are completely stationary.

The motion elements are useful because they can be organized to create nearly any shape, and that shape can appear to move in a particular direction even though the elements are still. A shape formed from the local elements is referred to as a global figure. For example, in FIG. 5, the motion elements are arranged in a circular pattern (the circle in this instance is the global figure). By modulating the luminance pattern of the elements, the whole circle will appear to rotate. The direction of rotation depends upon the relative modulation phase of the local elements. So, for example, if the elements are from FIG. 4A, and if the modulation of sub-element 3 leads sub-element 1 by 90 degrees, the ring rotates to the right; if the modulation of sub-element 3 trails sub-element 1 by 90 degrees, the ring rotates to the left. The sub-elements are small (sometimes as small as a single pixel). If an observer's acuity is good enough to resolve the pixel, the observer will see motion.

The described tests can manipulate a number of features of the illusory displays in order to assess visual function. These features are as follows: the size of the sub-elements or edges (the best observer would be able to see motion with one pixel); the contrast of modulation (the motion of the object is harder to see when the modulation contrast goes from light gray to dark instead of from white to black), the number of elements in the global object (the motion of the ring is easier to see when the elements are closer together), and the presence of other elements that do not create a global shape (the global motion tends to be easier to see in a field of noise).

The observer response can be measured through a number of different of devices (when tested on a regular monitor, response can be measured by, for example, a button response or the turning a steering wheel or other input device; in virtual environments, the observer could respond by moving in a particular direction or by reaching in one direction or another.

An illusory motion display affords a unique method for measuring an observer's response. The motion pattern created by the diamond illusion or by many global motion configurations compels the observer's eyes to follow the direction of motion even though all the elements remain stationary. The motion displays described above can therefore be presented while an eye-tracker takes measurements of observer response. There are many different types of eye-trackers, most of which record measurements that indicate the horizontal and vertical gaze direction. In the case of the diamond illusion, when the edges modulate in such a way that the diamond appears to move to the left, the observer's gaze would move leftward, thereby creating a change in the eye-tracker's measurement of horizontal position while keeping the measurement of the vertical position stationary. An analysis of the slope of the horizontal and vertical position data versus time can be used to predict the direction that the eye moved.

Therefore, eye-tracking technology can be used in conjunction with features described above to determine when an observer sees motion and when they can't. In this way, eye movements can be used to assess an observer's acuity without their knowing (or their being able to be aware) that their vision is being tested. Such a test would be useful for people wishing to deceive such a test, for people who are cognitively impaired, for infants, and for others who have trouble communicating.

In another aspect of the invention, the directional illusion is used as a simple, definitive assay for the measurement of visual performance, such as sensitivity to contrast and visual acuity. In one embodiment, to test for visual acuity, the width of the edges can be changed until the observer cannot correctly identify the direction of motion of the shape. Alternatively, the observer can move away from the screen until he/she cannot correctly identify the direction of motion. Acuity can be measured in general settings, such as a hospital, eldercare, workplace, or shopping mall, or in dynamic environments such as in a video game, a virtual reality environment, or in an active environment (such as with sports or military) where it might be advisable to measure acuity while observers participate in an activity; or mass screening in public health situations.

In another aspect of the invention, the display of the directional illusion can be presented to different ocular locations to test for visual acuity in the visual periphery; such tests can be useful, for example, for ocular screening in a department of motor vehicles.

In one embodiment, the described directional illusion permits an accurate determination of acuity and allows patients to more accurately perceive visual acuity than they can by use of static reflected or projected letters, symbols, or shapes, as used by the Snellen and similar tests. In an acuity test, a subject may be asked to indicate when the movement illusion is perceived. In one embodiment, the parameters of the directional illusion can be varied, as described above, until the subject indicates the perception of movement in the image. Alternatively, the parameters of the directional illusion can remain fixed, and the distance between the subject and the device displaying the directional illusion can be varied.

The acuity threshold, which is the perception of motion from a specific distance, correlates to the specific visual acuity. In viewing directional illusion images, the subject either sees the motion of the image because the viewing distance is close enough and the acuity is sufficient, or the patient does not see the motion because the distance is too far and the acuity is insufficient. Unlike the Snellen test, the subject does not need to be able to read English letters to identify the acuity threshold, to identify the direction of motion.

In one embodiment, the visual acuity test is viewed on a standard computer monitor or projected image at distances equivalent to and corresponding to the Snellen test.

In addition to the use of the described directional illusion in traditional-type visual assessments, the illusion can also be used in various settings. For example, the directional illusions could be used as a screening device for detecting visual problems over the internet, or for mass screening. One issue in public health is to assess when vision is poor in group situations quickly and efficiently (often, this form of assessment uses letters or illiterate tests). In one embodiment, the individuals to be assessed could move towards the screen displaying the illusion and state when they see the movement. The distance from the screen, size of the image, and other pertinent variables may be recorded.

The directional illusion could also be used in non-clinical settings. Human vision is an information-processing task. The human eyes are capable of looking at what is where, but the brain processes and generates a representation of this information in its profusion of color, form, motion and detail. The central vision (center of our retina) has the highest visual acuity and discriminative vision. Visual acuity decreases with distance from the fovea (the center of the retina) to the periphery. The combined field of view of our both eyes is approximately 180° with a 120° area of overlap. In general, the periphery is a larger low resolution field, and the central is a smaller high resolution field.

The central area or fovea subtends only for 2.5° of our visual field, but our head movements coupled with rapid saccadic eye movements give the impression that the combined field of view has a resolution similar to that of the foveal resolution (high resolution). The fovea also uses these saccadic eye movements to acquire peripheral targets. For example, if a viewer fixates foveal vision at the center of a large web page, the viewer will experience the illusion that the entire page is equally legible. It is only when we maintain our focus at the center of the web page and do not shift our eyes to the edge that we realize that the periphery is illegible.

By suppressing our natural tendency to turn our head or eyes, the peripheral regions of the retina can be trained to identify objects, thus improving the peripheral vision. This can be achieved by instructing the subject to stare at a visual marker that is intended for the subject to focus on using the central vision. While the subject is looking directly at the visual marker, a peripheral target is also displayed on the screen. The peripheral target is intended for identification using the peripheral vision of the subject, while the subject is directly looking at the visual marker. Identification of peripheral targets, in general, refers to recognizing characteristics of the target (i.e., visually discernable characteristics) in addition to detecting the presence of target. In the present case, the peripheral target is the described directional illusion, and the subject's task is to identify movement. This practicing task trains the subject to use visual activities to identify objects using the peripheral vision. This task also serves the purpose of assessing the subject's peripheral vision. In a further embodiment, the direction of movement of the illusion may be changed during testing, and the subject is asked to identify these changes.

The subject can engage in these visual activities using a portable device. For example, the visual mark and peripheral targets can be displayed in a video or an image on a computer screen, a laptop computer screen, a television set or screen, and/or portable device including but not limited to a mobile phone, an MP3 player, a Blackberry, a Palm Treo, a handheld computer, a head-mounted unit, and/or an iPhone, etc.

As further examples, the images of the directional illusion can be placed in sports video goggles or other head-mounted displays and used in various visual performance assessments and/or visual training. In another embodiment, monitors displaying the illusion can be placed in different locations around a testing environment, and observers can label the direction of motion in the displays. For example, a method for improving a subject's peripheral vision is to present the directional illusion on a display screen, where the displayed directional illusion is in the subject's peripheral vision. The subject would then be asked to correctly identify motion of the illusion using peripheral vision.

In other embodiments, the directional illusion could be inserted into a video game in which rewards, targets, or movement around or at an object depends upon correctly identifying the direction of motion in a diamond.

In further embodiments, the directional illusion can be used to customize displays of personal images. For example, the images could be provided by a user and the images could be modified or enhanced to introduce the illusion of movement into the image. The directional illusion can be used as a technique to direct attention to an image or as a marketing strategy or as way of enhancing a visual test.

In a further aspect, a method of drawing motion pixels on a display is provided. Users can specify the location and the direction indicated by the motion pixels so as to create global shapes of their choosing and adjust the components of the motion pixels to create motion in the direction of their choosing. In one embodiment, the motion pixels are placed on an already existing image so as to enhance the aesthetics of the image or to produce the illusion of motion in stationary objects in the images.

The invention claimed is:

1. A method for testing visual acuity in a subject, the method comprising
   i) creating a visual illusion of perpetual directional movement by
      (a) displaying to a subject, a stationary image comprising of an array of motion pixels comprising subelements, and enclosing a center shape or defining a global figure,
      (b) varying at least one component of the sub-elements selected from luminance levels, contrast, phase, modulation amplitude, width, or viewing distance between the subject and the sub-elements, to create the appearance of the perpetual motion in the center shape or global figure,
   ii) ascertaining whether the subject can perceive movement in the center shape or global figure, and
   iii) recording the subject's perception of motion or adjusting the features so as to null or change the perceived motion, to test the subject's visual acuity,
   wherein the image comprises motion pixels which are embedded in larger fields of motion pixels, where the field comprises multiple subsets, each subset correlated to create the perception of the perpetual motion and to define a moving shape in a field, such that a single shape moves in one direction, and other shapes move in other directions, and ascertaining whether the subject can identify the shape moving in a different direction from the other shapes.

2. The method of claim 1, wherein if the subject perceived motion, the subject's perception of the direction of motion is also determined, thereby obtaining a measure of the visual acuity and contrast sensitivity of the subject.

3. The method of claim 1, wherein the luminance levels, contrast, relative phase, modulation amplitude, width, or viewing distance of the sub-elements are varied systematically until the subject perceives, does not perceive, or reverses the direction of motion.

4. The method of claim 1 wherein the image is displayed on a monitor, virtual reality headset, mobile device, or projection device.

5. The method of claim 1, wherein based on the subject's feedback, at least one component of the sub-elements is further varied to change perceivability or direction of the motion of the global figure or enclosed shape.

6. The method of claim 1, further comprising the use of an eye-tracking device, where at least one of speed or direction of eye movement is used to indicate the direction of motion perceived by the subject.

7. The method of claim 6, wherein data obtained from the eye tracking device is correlated with the onset of, and/or any changes to, the image displayed to the subject.

8. The method of claim 1, wherein the image is presented in the visual periphery of the subject and the method tests visual characteristics of the subject's peripheral vision.

\* \* \* \* \*